(12) United States Patent
Moularat

(10) Patent No.: US 8,127,593 B2
(45) Date of Patent: Mar. 6, 2012

(54) METHOD FOR DETECTING FUNGAL CONTAMINATION

(75) Inventor: Stephane Moularat, Lognes (FR)

(73) Assignee: Centre Scientifique et Technique du Batiment (CSTB), Champs-sur-Marne (FR)

( * ) Notice: Subject to any disclaimer, the term of this patent is extended or adjusted under 35 U.S.C. 154(b) by 32 days.

(21) Appl. No.: 12/529,817

(22) PCT Filed: Mar. 4, 2008

(86) PCT No.: PCT/FR2008/050366
§ 371 (c)(1),
(2), (4) Date: Sep. 3, 2009

(87) PCT Pub. No.: WO2008/125770
PCT Pub. Date: Oct. 23, 2008

(65) Prior Publication Data
US 2010/0107740 A1    May 6, 2010

(30) Foreign Application Priority Data

Mar. 5, 2007  (FR) .................................... 07 01578

(51) Int. Cl.
*G01N 33/00* (2006.01)
(52) U.S. Cl. ......................... 73/31.03; 73/23.2
(58) Field of Classification Search ................ 436/145; 73/31.03, 23.2

See application file for complete search history.

(56) References Cited

OTHER PUBLICATIONS

International Search Report dated Oct. 6, 2008.
Anna-Sara Claeson et al., "Volatile metabolites from microorganisms grown on humid building materials and synthetic media", Journal of Environmental Monitoring, Oct. 2002, pp. 667-672, vol. 4, No. 5, The Royal Society of Chemistry, XP-002457027.
Pengfei Gao et al., "Determination of Unique Microbial Volatile Organic Compounds Produced by Five *Aspergillus* Species Commonly Found in Problem Buildings", AIHA Journal, Mar./Apr. 2002, pp. 135-140, vol. 63, No. 2, XP-009091499.
H. Schleibinger et al., "Emission patterns and emission rates of MVOC and the possibility for predicting hidden mold damage", Indoor Air, 2005, pp. 98-104, vol. 15, Suppl. 9, Blackwell Munksgaard, XP-002457026.
Hans Schleibinger et al., "Sind MVOC geeignete Indikatoren fur einen verdeckten Schimmelpilzbefall?", Umweltmedizin in Forschung and Praxis, 2004, pp. 151-162, vol. 9, No. 3, XP-009091599.
Robert Walinder et al., "Nasal Lavage Biomarkers: Effects of Water Damage and Microbial Growth in an Office Building", Archives of Environmental Health, 2001, pp. 30-36, vol. 56, XP-009091580.

*Primary Examiner* — Christine T Mui
(74) *Attorney, Agent, or Firm* — Young & Thompson

(57) ABSTRACT

A method for detecting a fungal contamination of an indoor environment by calculation of a chemical index of the fungal contamination. A sample of volatile organic compounds (VOCs) is withdrawn in indoor surroundings, and the presence or absence of certain predetermined VOCs resulting from fungal metabolism is detected.

7 Claims, 2 Drawing Sheets

METHOD FOR DETECTING FUNGAL CONTAMINATION

FIELD OF THE INVENTION

Figure 1:
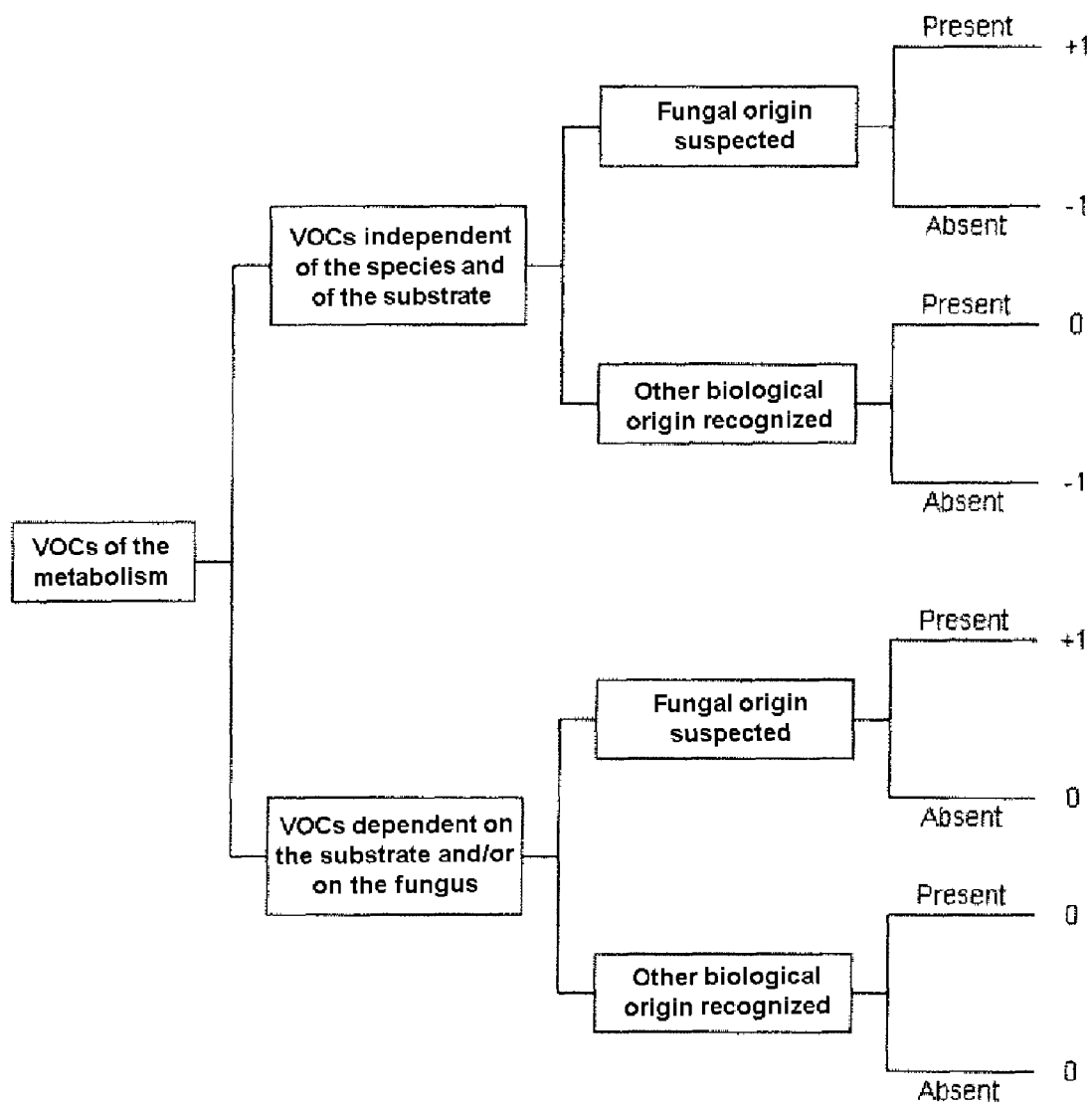

The present invention relates to a method for detecting fungal contamination in indoor surroundings.

BACKGROUND OF THE INVENTION

Indoor surroundings is understood to mean a confined space inside a building which is not continuously aerated. Examples of indoor surroundings can be found in dwellings, museums, churches, cellars, historic monuments, administrative buildings, schools, and hospitals.

Since the 1970s and the first oil crisis, the energy saving policy implemented has resulted in containment of dwellings with in particular the increased insulation of buildings. This policy, in combination with the spread of household appliances which generate vapor, such as washing machines and tumble dryers, has had the consequence of an increase in relative humidity favorable to the growth of microorganisms, in particular molds, on the majority of substrates, such as building materials.

The premises are then capable of forming "ecological niches" for the growth of microorganisms of this type. This phenomenon has thus been reflected by an increase in the number of premises contaminated by molds over the last thirty years.

The presence of molds in indoor surroundings is not without health consequences. This is because numerous studies have demonstrated their role both in the decomposition of the materials and works which they colonize and in the appearance of symptoms in the occupants of premises in which molds are present.

During the last two decades, numerous studies carried out in North America and Europe have demonstrated that, under some exposure circumstances, these microorganisms may be responsible for the appearance of diseases, in particular respiratory diseases, such as allergies, infections or toxin-derived infections.

Currently, the techniques used to detect the presence of molds in indoor surroundings are based on the visual recognition of fungal growth and the culturing of conidia withdrawn from the air or from the surfaces. In point of fact, the presence of these microorganisms can prove to be difficult to diagnose in the case of "masked" contaminations where the spores are not given off into the surroundings (when the contaminations occur in the ventilation system or also in the structures of the building, for example). While then invisible at the surface of the building materials and undetectable by microbiological analysis of the air, the molds nevertheless continuously produce metabolites and decomposition products which can be inhaled and which are responsible in some cases for diseases.

Moreover, the response of these measurement techniques is lengthy since it is necessary to wait for the microorganisms withdrawn to be grown in the laboratory before being able to carry out the analysis.

An object of the present invention is thus to overcome all or part of the abovementioned disadvantages.

SUMMARY OF THE INVENTION

Fungi give off, from the beginning of the growth thereof, volatile molecules (Volatile Organic Compounds) resulting either from their metabolism or from the decomposition of the material on which they are growing by the enzymes or acids which they produce. In contrast to the spores, these compounds disperse in the surroundings without being retained by the substrates. Consequently, the detection of some of these compounds, which are specific for one or more fungal species, makes it possible, on the one hand, to identify a contamination from the beginning of the growth of the fungi and, on the other hand, to detect "masked" contaminations where the spores have not been given off into the surroundings.

The Applicant Company has now found that some VOCs are present in the ambient air only in the presence of molds. These VOCs thus specifically result from fungal metabolism. The Applicant Company has also found that some other VOCs are present in the ambient air not only in the presence of molds but also in the presence of some building materials or also of other biological contaminations, such as bacterial contaminations. An example of such a bacterial contamination is geosmin, which is given off both by molds and by bacteria. Armed with this discovery, the Applicant Company has been able to demonstrate that these VOCs resulting specifically from fungal metabolism can be divided into two groups:
- the VOCs which are given off independently of the fungal species and of the substrate on which the fungal species is growing, and
- the VOCs which are given off as a function of the fungal species and/or of the substrate on which it is growing.

A distinction is made, among the VOCs which are given off independently of the fungal species and of its substrate, between the VOCs which are given off only by fungal species and the VOCs which can have other biological origins.

The Applicant Company has thus determined three distinct categories of fungal VOCs. The detection of these VOCs forms the basis of the invention. Thus it is to the credit of the Applicant Company that, after lengthy and detailed research studies, it has developed a method for detecting fungal contamination in indoor surroundings which makes possible the detection of such a fungal contamination even in the absence of visible signs of contamination.

Thus, the method for detecting fungal contamination of indoor surroundings according to the invention comprises the following stages:
a. withdrawing a sample of volatile organic compounds (VOCs) in indoor surroundings,
b. detecting the presence or the absence of certain predetermined VOCs resulting from fungal metabolism, these predetermined VOCs comprising at least one VOC of each of the three following categories of VOCs:
  (1) VOCs which are given off independently of the fungal species and of their substrate and which are given off only by fungal species;
  (2) VOCs which are given off independently of the fungal species and of the substrate but which can also have other biological origins; and
  (3) VOCs which are given off according to the fungal species and/or substrate;
c. calculating a chemical index for fungal contamination according respectively to the presence and absence of the predefined VOCs resulting from fungal metabolism.

BRIEF DESCRIPTIONS OF THE DRAWINGS

FIG. 1 represents diagrammatically the method of incrementation for calculating the contamination index as a function of the presence or the absence of each VOC.

Figure 2:
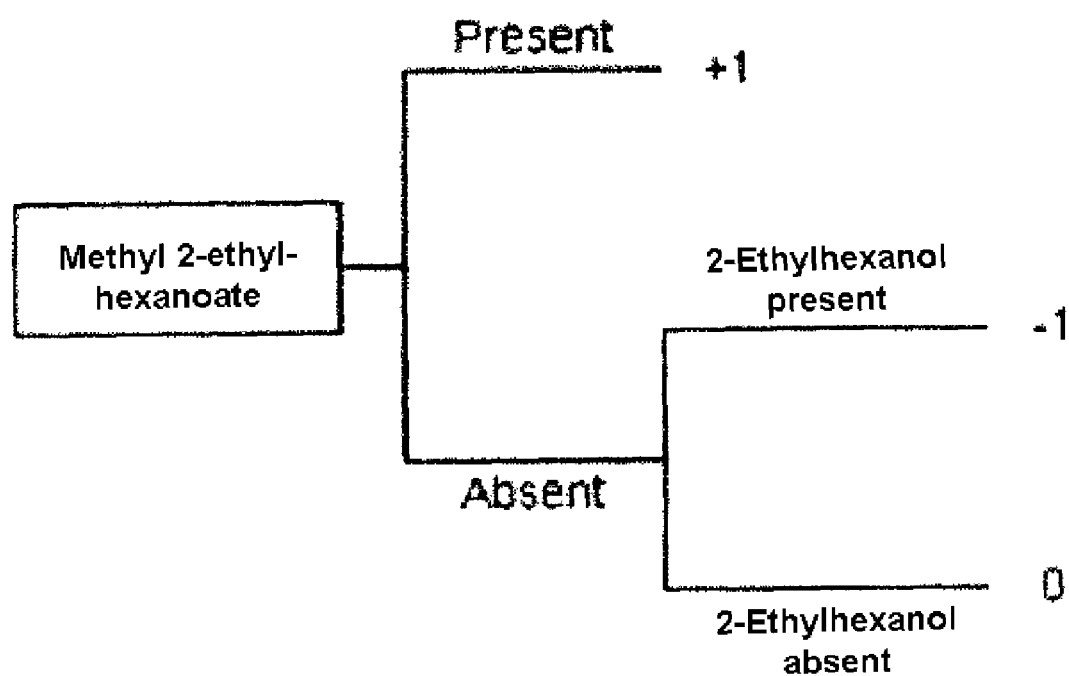

FIG. 2 describes the method of incrementation for calculating the contamination index as applied to methyl 2-ethylhexanoate.

DETAILED DESCRIPTION OF THE INVENTION

The VOCs which are given off only by fungal species and the emission of which is independent of the substrate comprise in particular 1-octen-3-ol, 1,3-octadiene and methyl 2-ethylhexanoate. The VOCs which can also have other biological origins, the emission of which is independent of the substrate, comprise 2-methylfuran, 3-methylfuran, 3-methyl-1-butanol, 2-methyl-1-butanol and α-pinene. The VOCs which are given off according to the fungal species and/or the substrate comprise in particular 2-heptene, dimethyl sulfide, 4-heptanone, 2(5H)-furanone, 3-heptanol and methoxybenzene.

In one embodiment, the predetermined VOCs also comprise 2-ethylhexanol, in addition to the VOCs of categories (1), (2) and (3).

In accordance with the method of the invention, stage a) of withdrawing the VOC sample is preferably carried out by diffusive sampling over a solid adsorbent of the type of CARBOGRAPH 4®(graphitized carbon black).

From the VOC sample withdrawn in stage a), the presence or the absence of certain predetermined VOCs resulting from fungal metabolism is detected. These predetermined VOCs comprise at least
one VOC which is given off independently of the fungal species and of its support and which is given off only by fungal species;
one VOC which is given off independently of the fungal species and of the substrate but which can also have other biological origins; and
one VOC which is given off according to the fungal species and/or the substrate.

By detecting the presence or the absence of at least one VOC of each of the three abovementioned categories of VOCs, the certainty of the detection method according to the invention is increased in comparison with a detection of the presence or the absence of VOCs resulting from just one of these categories.

Preferably, several VOCs of each of the three abovementioned categories will be detected.

In an advantageous embodiment, the VOCs of category (1) are chosen from the group consisting of 1-octen-3-ol, 1,3-octadiene and methyl 2-ethylhexanoate, the VOCs of category (2) are chosen from the group consisting of 2-methylfuran, 3-methylfuran, 3-methyl-1-butanol, 2-methyl-1-butanol and α-pinene, and the VOCs of category (3) are chosen from the group consisting of 2-heptene, dimethyl sulfide, 4-heptanone, 2(5H)-furanone and 3-heptanol.

Preferably, the predetermined VOCs are detected by gas chromatography followed by mass spectrometry (GC/MS).

After the detection of the presence or the absence of each of the predetermined VOCs, a chemical index for fungal contamination is calculated. This calculation is based on the following observations, which the Applicant Company was able to make after lengthy and detailed research studies.

The presence of VOCs resulting specifically from fungal metabolism which are given off independently of the fungal species and of its substrate and which are given off only by fungal species directly indicates the presence of fungal contamination, while the absence of such VOCs indicates the absence of fungal contamination.

In contrast, the presence of VOCs resulting from fungal metabolism which can also have other biological origins does not allow it to be concluded that fungal contamination is present. However, the absence of such VOCs indicates the absence of fungal contamination.

As regards the VOCs resulting specifically from fungal metabolism but which are given off according to the fungal species and/or the substrate, their presence indicates the presence of fungal contamination while their absence does not allow it to be concluded that fungal contamination is absent.

A specific case is methyl 2-ethylhexanoate, which is fundamentally among the VOCs given off independently of the fungal species and of its substrate but the formation of which appears to be due to the conversion of 2-ethylhexanol by the mold. Without wishing to be committed to any one theory, it is assumed that the 2-ethylhexanol is converted to methyl 2-ethylhexanoate via an oxidation reaction to give 2-ethylhexanoic acid, which is subsequently esterified to give methyl 2-ethylhexanoate. The presence of methyl 2-ethylhexanoate allows it to be concluded that fungal contamination is present. On the other hand, in the case of the absence of methyl 2-ethylhexanoate, it is important to detect the presence or the absence of 2-ethylhexanol. If, in this case, 2-ethylhexanol is present, it may be concluded that fungal contamination is absent. If, on the other hand, 2-ethylhexanol is absent, it is not possible to conclude that fungal contamination is present.

On the basis of these observations, it is to the credit of the Applicant Company that it has developed a method for calculating a chemical index for fungal contamination which is based on the following incrementation. The presence of a VOC is incremented with a value "1" if the presence of the VOC indicates the presence of fungal contamination and with a value "0" if the presence of the VOC does not allow it to be concluded that fungal contamination is present. The absence of a VOC is incremented with a value "−1" if the absence of the VOC indicates the absence of fungal contamination and with a value "0" if the absence of the VOC does not allow it to be concluded that fungal contamination is absent. The incrementation principles are summarized in table 1 below.

TABLE 1

| | Incrementation | |
|---|---|---|
| VOC | Presence | Absence |
| Given off independently of the fungal species and of its substrate, given off only by fungal species | 1 | −1 |
| Given off independently of the fungal species and of the substrate, can also have other biological origins | 0 | −1 |
| Given off according to the fungal species and/or the substrate | 1 | 0 |

In the specific case of methyl 2-ethylhexanoate, the presence of methyl 2-ethylhexanoate is incremented with a value "1", while its absence is incremented with a value "−1" if 2-ethylhexanol is present in the sample and with a value "0" if 2-ethylhexanol is absent from the sample. The incrementation principle with respect to methyl 2-ethylhexanoate is summarized in table 2.

TABLE 2

Methyl 2-ethylhexanoate incrementation

| VOC | Presence | Incrementation Absence | |
|---|---|---|---|
| | | 2-Ethylhexanol present | 2-Ethylhexanol absent |
| Methyl 2-ethylhexanoate | 1 | −1 | 0 |

The chemical index for fungal contamination is calculated by addition of the increments which were assigned to the presence or to the absence of each of the predetermined VOCs. The result of this addition, that is to say the chemical index for fungal contamination, is thus either a negative value or a value equal to zero or a positive value. If the chemical index for fungal contamination is a value of less than or equal to 0, this indicates the absence of fungal contamination. An index for fungal contamination which is strictly positive indicates the presence of fungal contamination.

The method for detecting fungal contamination according to the invention is particularly useful for the early detection of such contamination, that is to say before the appearance of visible signs of contamination. This possibility of early detection is, for example, of great importance in historical monuments, churches or museums, where irreparable damage has in general already been caused when the first visible signs of fungal contamination become apparent.

The following exemplary embodiments illustrate the present invention without in any way limiting the scope thereof.

EXAMPLE 1

Withdrawing a VOC Sample in Indoor Surroundings

VOC withdrawals in situ were carried out by diffusive sampling over a solid adsorbent of the type of CARBOGRAPH 4®(graphitized carbon black) in twelve housing units. Five of the twelve housing units comprised at least one room having a visible mold stain of greater than 1 m$^2$ (dwellings 1 to 5) and seven of the twelve housing units did not exhibit visible signs of fungal contamination (dwellings 7 to 12). Withdrawing is provided by a diffusion tube. The sampler is composed of a cartridge, of a diffusive body and of an adapter.

The cartridge is cylindrical (40-60 mesh s.s. net), with an external diameter of 4.8 mm, and contains 300 mg of graphitized carbon the type of CARBOGRAPH 4®(graphitized carbon black). This cartridge is placed before the withdrawing in a diffusive body made of polyethylene. The combination is subsequently screwed onto a rack using a clipable support.

The passive tubes are exposed on site for a time of 7 days. The withdrawing point is situated at a height of between 0.5 and 1 m. After exposure, the cartridges are stored in a refrigerator before analysis.

The majority of the VOCs (fungal or nonfungal) composing the air of the housing unit are then trapped in the adsorbent.

EXAMPLE 2

Detection of the Presence or the Absence of Certain VOCs

The tubes containing the adsorbent are transferred into a laboratory analytical line. This line consists of a combination of three techniques:
 gas chromatography (GC), used to separate the VOCs,
 flame ionization (FID), which makes it possible to detect the various molecules,
 mass spectrometry (MS), employed to identify these compounds.

Chromatograms are thus obtained for each of the twelve housing units and are examined for the presence of the specific VOCs therein (see table I for the VOCs looked for).

EXAMPLE 3

Calculation of the Chemical Index for Fungal Contamination

A contamination index is subsequently calculated in order to collate all the information provided by the presence or the absence of the specific VOCs identified.

In order to formalize the set of observations made on the origin of these molecules, the index is calculated as a function of the presence or of the absence of each of these VOCs. The method of incrementation of this index is represented diagrammatically in FIG. 1.

As regards methyl 2-ethylhexanoate, it has been taken into account that the formation thereof might be due to the conversion of 2-ethylhexanol by the mold. The incrementation rule which has been applied in this case is described in FIG. 2.

According to the construction of this index, a high value renders probable the presence of fungal growth; in contrast, a low value excludes it.

Thus, an index value of strictly greater than 0 allows it to be concluded that fungal growth is present in the housing unit studied, while a negative or zero value rules out the presence thereof.

The results of the analysis of the chromatograms of the withdrawals carried out in the 12 housing units are referenced in table I.

TABLE I

List of the VOCs resulting from metabolism identified in 12 dwellings

| Compound | Dwelling with visible contamination | | | | | Dwelling without visible contamination | | | | | | |
|---|---|---|---|---|---|---|---|---|---|---|---|---|
| | Dwe. 1 | Dwe. 2 | Dwe. 3 | Dwe. 4 | Dwe. 5 | Dwe. 6 | Dwe. 7 | Dwe. 8 | Dwe. 9 | Dwe. 10 | Dwe. 11 | Dwe. 12 |
| 1-Octen-2-ol | 0 | 0 | 0 | 0 | 1 | 0 | 0 | 0 | 0 | 0 | 0 | 0 |
| 1,3-octadiene | 1 | 1 | 1 | 1 | 1 | 1 | 0 | 0 | 1 | 1 | 1 | 0 |
| Methyl 2-ethylhexanoate | 0 | 0 | 0 | 0 | 0 | 0 | 0 | 0 | 0 | 0 | 0 | 0 |
| 2-Ethylhexanol | 1 | 1 | 1 | 1 | 1 | 1 | 1 | 1 | 1 | 1 | 1 | 1 |
| α-Pinene | 1 | 1 | 1 | 1 | 1 | 1 | 1 | 1 | 1 | 1 | 1 | 1 |
| 2-Methylfuran | 1 | 1 | 1 | 1 | 1 | 0 | 0 | 1 | 1 | 1 | 1 | 0 |
| 3-Methyl-1-butanol | 1 | 0 | 1 | 1 | 1 | 1 | 1 | 1 | 1 | 1 | 1 | 1 |

TABLE I-continued

List of the VOCs resulting from metabolism identified in 12 dwellings

| Compound | Dwelling with visible contamination | | | | | Dwelling without visible contamination | | | | | | |
|---|---|---|---|---|---|---|---|---|---|---|---|---|
| | Dwe. 1 | Dwe. 2 | Dwe. 3 | Dwe. 4 | Dwe. 5 | Dwe. 6 | Dwe. 7 | Dwe. 8 | Dwe. 9 | Dwe. 10 | Dwe. 11 | Dwe. 12 |
| 2-Methyl-1-butanol | 0 | 0 | 0 | 0 | 0 | 0 | 0 | 0 | 0 | 0 | 0 | 0 |
| Dimethyl disulfide | 1 | 1 | 1 | 0 | 0 | 0 | 0 | 0 | 1 | 0 | 0 | 0 |
| 2-Heptene | 1 | 1 | 1 | 1 | 1 | 0 | 0 | 0 | 1 | 1 | 1 | 1 |
| 2-Methylisoborneol | 0 | 0 | 0 | 0 | 0 | 0 | 0 | 0 | 0 | 0 | 0 | 0 |
| Sesquiterpene A | 0 | 0 | 0 | 0 | 0 | 0 | 0 | 0 | 0 | 0 | 0 | 0 |
| Sesquiterpene B | 1 | 1 | 0 | 1 | 1 | 0 | 1 | 0 | 1 | 0 | 0 | 0 |
| Sesquiterpene C | 0 | 0 | 0 | 1 | 0 | 0 | 0 | 0 | 0 | 0 | 0 | 0 |
| Terpenoid | 0 | 0 | 0 | 0 | 0 | 0 | 0 | 0 | 0 | 0 | 0 | 0 |
| 4-Heptanone | 1 | 1 | 1 | 0 | 0 | 0 | 0 | 0 | 0 | 0 | 0 | 0 |
| 3-Heptanol | 0 | 0 | 0 | 0 | 0 | 0 | 0 | 0 | 0 | 0 | 0 | 0 |
| Methoxybenzene | 0 | 0 | 0 | 0 | 0 | 0 | 0 | 0 | 0 | 0 | 0 | 0 |
| 2(5H)-Furanone | 1 | 1 | 0 | 1 | 0 | 0 | 0 | 0 | 0 | 0 | 0 | 0 |

(0 = absence of the compound, 1 = presence of the compound)

α-Pinene and 3-methyl-1-butanol are found to be systematically present. This observation confirms the hypothesis that these compounds have numerous sources of emission (molds, bacteria, plants).

The contamination index established was subsequently applied for each dwelling (see FIGS. 1 and 2). The values of this index are listed in table II.

TABLE II

Values of the indices assigned to each dwelling

| Dwelling with visible contamination | Value of the index | Dwelling without visible contamination | Value of the index |
|---|---|---|---|
| D1 | 4 | D6 | −3 |
| D2 | 3 | D7 | −4 |
| D3 | 2 | D8 | −3 |
| D4 | 3 | D9 | 2 |
| D5 | 3 | D10 | 0 |
| | | D11 | 0 |
| | | D12 | −4 |

The dwellings exhibiting visible contamination all have a strictly positive indicator. This positive value of the index thus confirms the probable presence of fungal growth in these dwellings.

With the exception of dwelling No. 9, the dwellings without visible contamination have indicators of less than or equal to 0. The value of the indices is thus correlated with the presence of fungal growth.

Dwelling No. 9, categorized in the a priori "healthy" housing units, behaves, in terms of chemical tracers, in the same way as the dwellings for which fungal contamination is established (indicator strictly greater than 0). These dwellings thus do not exhibit a risk of fungal contamination.

In order to confirm these hypotheses, these results were combined with a questionnaire submitted to the occupants of each dwelling. Among the various questions, six could be associated with the presence of our tracers. These questions and the associated replies for each dwelling are listed in table III.

TABLE III

Results of the questionnaire submitted to the proprietors of the twelve dwellings

| | Molds visible over more than 1 m$^2$ | Presence of dampness in the dwelling | Infiltration of water during the last 12 months | Treatment against dampness | Presence of plants | Musty smell detected by the interviewers |
|---|---|---|---|---|---|---|
| Dwelling 1 | 1 | 1 | 0 | 0 | 0 | 1 |
| Dwelling 2 | 1 | 1 | 1 | 0 | 1 | 1 |
| Dwelling 3 | 1 | 1 | 1 | 1 | 1 | 1 |
| Dwelling 4 | 1 | 1 | 1 | 0 | 1 | 0 |
| Dwelling 5 | 1 | 1 | 1 | 0 | 1 | 0 |
| Dwelling 6 | 0 | 0 | 0 | 0 | 1 | 0 |
| Dwelling 7 | 0 | 0 | 0 | 0 | 1 | 0 |
| Dwelling 8 | 0 | 0 | 0 | 0 | 1 | 0 |
| Dwelling 9 | 0 | 0 | 1 | 0 | 1 | 0 |
| Dwelling 10 | 0 | 0 | 0 | 0 | 0 | 0 |
| Dwelling 11 | 0 | 0 | 0 | 0 | 1 | 0 |
| Dwelling 12 | 0 | 0 | 0 | 0 | 1 | 0 |

(1 = yes, 0 = no)

It is found that dwelling No. 9 (without visible sign but with a positive index) experienced infiltration of water during the 12 months preceding the withdrawing of VOCs. It is probable that this infiltration resulted in fungal contamination which was not detected visually.

Consequently, the index established made it possible to detect contamination before the appearance of the first visible traces of fungal growth.

What is claimed is:

1. A method for detecting fungal contamination of indoor surroundings according to the invention, which comprises the following stages:
   a. withdrawing a sample of volatile organic compounds (VOCs) in indoor surroundings,
   b. detecting the presence or the absence of certain predetermined VOCs resulting from fungal metabolism, the predetermined VOCs comprising at least one VOC of each of the three following categories of VOCs:
      (1) the VOCs which are given off independently of the fungal species and of its substrate and which are given off only by fungal species;
      (2) the VOCs which are given off independently of the fungal species and of the substrate but which can also have other biological origins;
      (3) the VOCs which are given off according to the fungal species and/or substrate;
   c. assigning for each predetermined VOC, a first figure if the VOC is present or a second figure if the VOC is absent, and calculating a chemical index for fungal contamination according respectively to all of the first figures for the presence and all of the second figures for the absence of the predetermined VOCs resulting from fungal metabolism.

2. The method for detecting fungal contamination as claimed in claim 1, wherein the presence or the absence of several VOCs of each of the three VOC categories is detected.

3. The method for detecting fungal contamination as claimed in claim 1, wherein the predetermined VOCs also comprise 2-ethylhexanol, in addition to the VOCs of categories (1), (2) and (3).

4. The method for detecting fungal contamination as claimed in claim 1, wherein
   the VOCs of category (1) are chosen from the group consisting of 1-octen-3-ol, 1,3-octadiene and methyl 2-ethylhexanoate,
   the VOCs of category (2) are chosen from the group consisting of 2-methylfuran, 3-methylfuran, 3-methyl-1-butanol, 2-methyl-1-butanol and $\alpha$-pinene,
   the VOCs of category (3) are chosen from the group consisting of 2-heptene, dimethyl sulfide, 4-heptanone, 2(5H)-furanone and 3-heptanol.

5. The method for detecting fungal contamination as claimed in claim 1, wherein, in stage c), for each of the predetermined VOCs, a figure of $-1$, 0 or 1 is assigned to as the first figure or the second figure, and the sum of these figures is the calculated chemical index for fungal contamination.

6. The method for detecting fungal contamination as claimed in claim 5, wherein, for each of the VOCs, with the exception of methyl 2-ethylhexanoate, the first and the second figures are assigned in the following way:
   the presence of VOC of category (1) is assigned a first figure of 1 and the absence of VOC of category (1) is assigned a second figure of $-1$;
   the presence of VOC of category (2) is assigned a first figure of 0 and the absence of VOC of category (2) is assigned a second figure of $-1$;
   the presence of VOC of category (3) is assigned a first figure of FIG. 1 and the absence of VOC of category (3) is assigned a second figure of 0.

7. The method for detecting fungal contamination as claimed in claim 5, wherein, for methyl 2-ethylhexanoate, the figures are assigned in the following way:
   the presence of methyl 2-ethylhexanoate is assigned a first figure of 1;
   the absence of methyl 2-ethylhexanoate is assigned a second figure of 0, if the absence of 2-ethylhexanol is detected, and assigned a second figure of $-1$, if the presence of 2-ethylhexanol is detected.

* * * * *